United States Patent [19]

Mewshaw

[11] Patent Number: 5,670,667
[45] Date of Patent: Sep. 23, 1997

[54] CHROMAN-2-YLMETHYLAMINO DERIVATIVES

[75] Inventor: Richard E. Mewshaw, South Brunswick, N.J.

[73] Assignee: American Home Products Corporation, Madison, N.J.

[21] Appl. No.: 630,794

[22] Filed: Apr. 10, 1996

[51] Int. Cl.$^6$ .................................. C07D 311/04
[52] U.S. Cl. ................................................ 549/407
[58] Field of Search .................... 549/407; 514/456

[56] References Cited

U.S. PATENT DOCUMENTS

| | | | |
|---|---|---|---|
| 4,321,270 | 3/1982 | Sundeen | 424/267 |
| 5,126,367 | 6/1992 | Stack et al. | 514/452 |
| 5,137,901 | 8/1992 | Junge et al. | 514/373 |
| 5,318,988 | 6/1994 | Schohe-Loop et al. | 514/458 |
| 5,371,094 | 12/1994 | Heine et al. | 514/323 |

FOREIGN PATENT DOCUMENTS

| | | | |
|---|---|---|---|
| 0325964 | 8/1989 | European Pat. Off. | 514/373 |
| 0334429 | 9/1989 | European Pat. Off. | 514/323 |
| 0369874 | 5/1990 | European Pat. Off. | 514/373 |
| 9505383 | 2/1995 | WIPO | 514/373 |

OTHER PUBLICATIONS

Indian Journal of Chemistry, 20B, 12, 1063–1067, Dec. 1981, Pratap et al.

*Primary Examiner*—Joseph McKane
*Attorney, Agent, or Firm*—Richard K. Jackson

[57] ABSTRACT

Compounds of the formula:

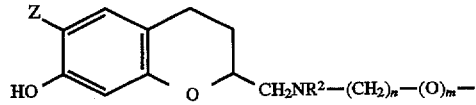

in which Z is hydrogen or a halogen; n is one of the integers 1, 2, 3, or 4; m is one of the integers 0 or 1; R is a substituted or unsubstituted aryl group in which the substituents are, independently, one or two members selected from the group consisting of alkyl, hydroxy, halo or amino groups; $R^2$ is hydrogen or alkyl; or a pharmaceutically acceptable salt thereof, are inhibitors of dopamine synthesis and release, useful in the treatment of schizophrenia, Parkinson's Disease, Tourette's Syndrome, alcohol addiction, cocaine addiction, and addiction to analagous drugs.

20 Claims, No Drawings

CHROMAN-2-YLMETHYLAMINO DERIVATIVES

RELATED APPLICATIONS

This application is a continuation-in-part of Provisional application Ser. No. 60/001,419, filed Jul. 25, 1995, by Richard E. Mewshaw.

BACKGROUND OF INVENTION

Efforts to induce antipsychotic activity with dopamine autoreceptor agonists have been successful (Corsini et al. Adv. Biochem. Psychopharmacol 16, 645–648, 1977; Tamminga et al. Science 200, 567–568, 1978; and Tamminga et al. Psychiatry 398–402, 1986). A method for determining intrinsic activity at the dopamine $D_2$ receptor was recently reported [Lahti et al., Mol. Pharm. 42, 432–438, (1993)]. Intrinsic activity is predicted using the ratio of the "low-affinity agonist" (LowAg) state of the receptor and the "high-affinity agonist" (HighAg) state of the receptor, i.e. LowAg/HighAg. These ratios correlate with the agonist, partial agonist, and antagonist activities of a given compound, which activities characterize a compounds ability to elicit an antipsychotic effect.

DESCRIPTION OF THE INVENTION

In accordance with this invention, there is provided a group of compounds which are useful antipsychotic agents. The compounds of this invention are essentially free from extrapyramidal side effects (EPS). The compounds of this invention are selective autoreceptor agonists, functioning primarily to activate only autoreceptors versus postsynaptic $D_2$ dopamine receptors. As such, they provide functional modulation of dopamine systems of the brain without the excessive blockade of the postsynaptic dopamine receptors, which have been observed to be responsible for the serious side effects frequently exhibited by agents found otherwise clinically effective for treatment of schizophrenia. Activation of the dopamine autoreceptors results in reduced neuronal firing a well as inhibition of dopamine synthesis and release and therefore provide a means of controlling hyperactivity of the dopaminergic systems.

More specifically, the compounds of this invention are depicted by the following Formula I:

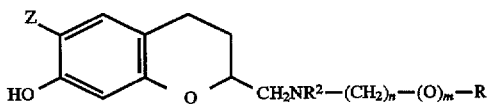

in which

Z is hydrogen or a halogen;

n is one of the integers 1, 2, 3, or 4;

m is one of the integers 0 or 1; and

R is a substituted or unsubstituted, phenyl or naphthyl group in which the substituents are, independently, one or two members selected from the group consisting of alkyl of 1 to 6 carbon atoms, hydroxy, halo or amino groups;

$R^2$ is hydrogen or alkyl of 1 to 6 carbon atoms; or a pharmaceutically acceptable salt thereof.

The preferred members representing R are:

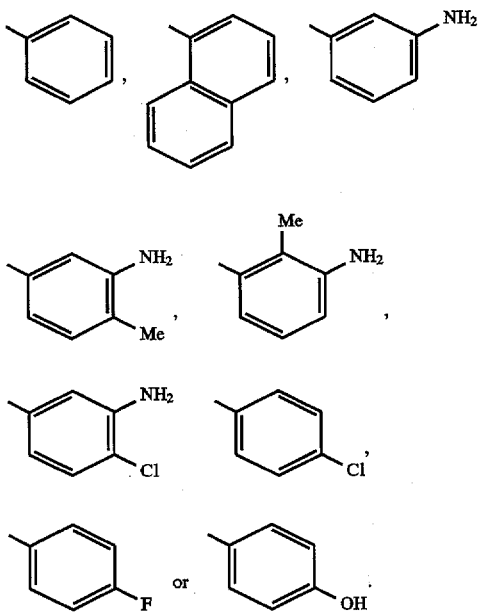

The pharmaceutically acceptable salts are those derived from such organic and inorganic acids as: acetic, lactic, citric, fumaric, tartaric, succinic, maleic, malonic, oxalic, hydrochloric, hydrobromic, phosphoric, nitric, sulfuric, methanesulfonic, methylbenzene sulfonic, and similarly known acceptable acids. The halogen represented by Z is chlorine, bromine, flourine or iodine. The compounds of this invention contain an asymmetric carbon atom and therefore appear as racemic mixtures which are readily resolved into their pure enantiomers by conventional means.

The compounds of Formula I are prepared by the overall reaction sequence as follows:

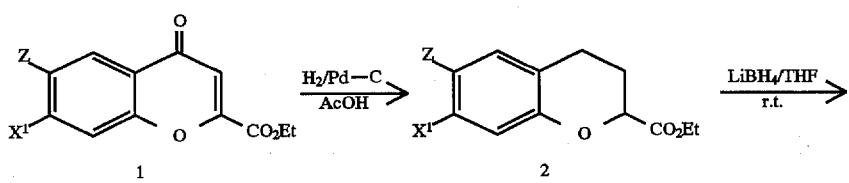

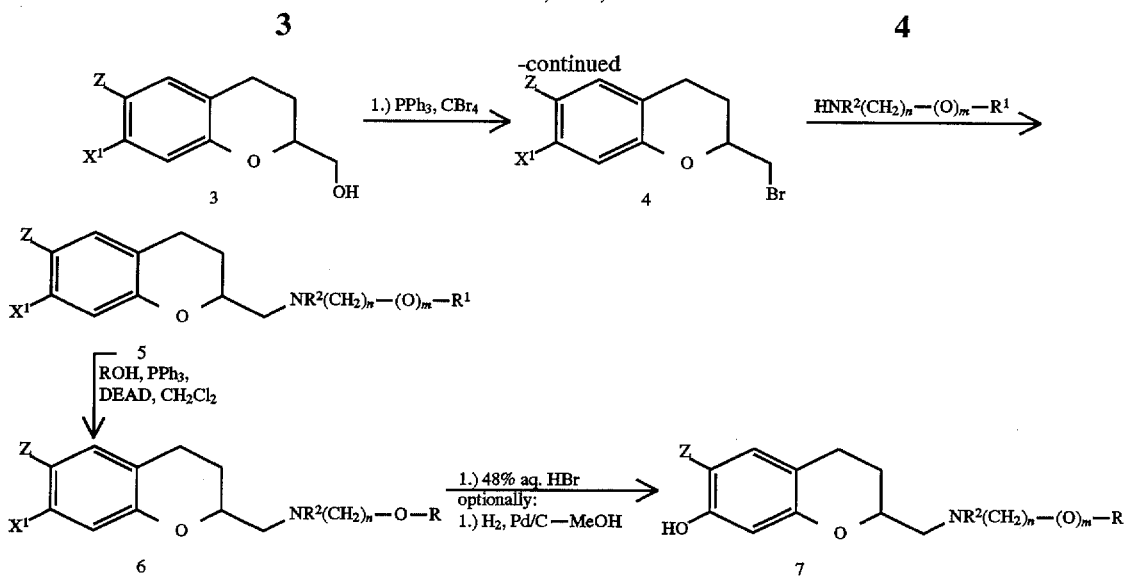

In this reaction sequence, $X^1$ is protected oxygen in which the protecting group is methyl, benzyl, and the like, known oxygen protecting groups. The final step of the reaction sequence, from compounds 5 or 6 to 7, involves deprotection of oxygen to provide the hydroxy group in 7-position of the benzopyran ring. The group $R^1$ is hydrogen or R (as defined above). The reaction sequence followed when $R^1$ is hydrogen and m is 1, proceeds via compound 6, whereas deprotection of compound 5, when $R^1$ is R and m is 1, proceeds directly to compound 7 by deprotection.

The compounds of this invention, where Z is a halogen, may also be prepared by the following procedure:

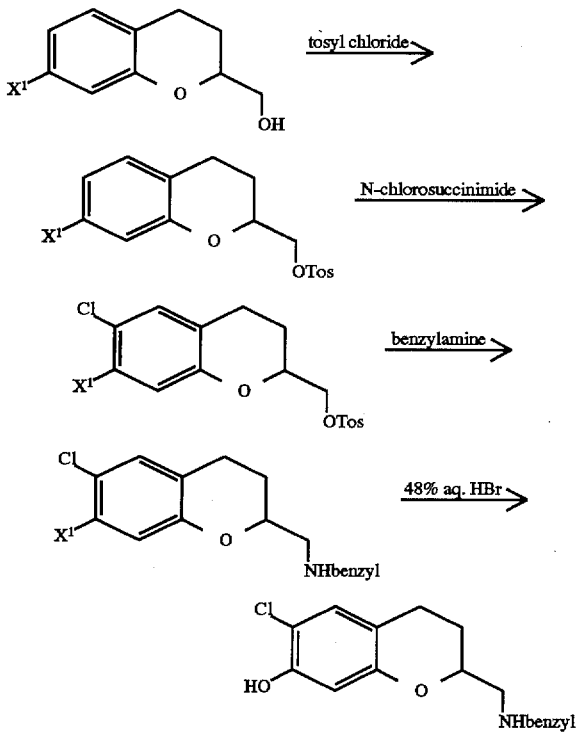

Again, $X_1$ represents the protected oxygen as discussed above.

Specific exemplification of the production of representative compounds of this invention is given in the following procedures:

Intermediate 1

Ethyl (R,S)-3,4-Dihydro-7-methoxy-2H-1-benzopyran-2-carboxylate

A solution of ethyl 7-methoxy-4-oxo-4H-1-benzopyran-2-carboxylate [prepared from 1-hydroxy-5-methoxy-acetophenone according to Appleton et al. J. Med. Chem. 20, 371–379, (1989)] in acetic acid (200 ml) was hydrogenated over 10% palladium on carbon at room temperature at 50 psi for 5 days. The reaction mixture was filtered through celite and the solvent was removed under vacuum. The product crystallized and was then triturated with 1:1 ethyl acetate-hexane to afford 20 g (72% yield) of product, mp 63°–64 ° C.; MS (EI) m/e 236 (M+).

Elemental Analysis for $C_{13}H_{16}O_4$ Calc'd: C, 66.09; H, 6.83 Found: C, 65.65; H, 6.76

Intermediate 2

(R,S)-3,4-Dihydro-7-methoxy-2H-1-benzopyran-2-methanol (R,S)-3,4-Dihydro-7-methoxy-2H-1-benzopyran-2-carboxylic acid ethyl ester (20 g) was dissolved in tetrahydrofuran (215 mL) and a 2.0M solution of lithium borohydride (100 mL, 0.20 moles) was added over 0.5 hour. After two hours the reaction was complete and the excess lithium borohydride was destroyed by the cautious addition of methanol. The reaction mixture was then diluted with ethyl acetate and washed with water. The organic layer separated and dried under vacuum to afford 16 g (96% yield) of a clear oil: IR ($CDCl_3$) 3600, 3450, 2920, 1620, 1585, and 1510 $cm^{-1}$; MS (EI) m/e, 194 (M+); $^1H$ NMR ($CDCl_3$) δ 1.75–1.94 (2H, m), 2.08 (1H, bs), 2.67–2.84 (2H, m), 3.74–3.86 (2H, m), 3.76 (3H, s), 4.09 (1H, m), 6.40 (1H, d, J=2.6 Hz), 6.46 (1H, dd, J=8.35, 2.64 Hz), 6.94 (1H, d, J=8.35 Hz).

Intermediate 3

(R,S)-3,4-Dihydro-7-(phenylmethoxy)-2H-1-benzopyran-2-methanol

This compound was prepared from (R,S)-3,4-dihydro-7-(phenylmethoxy)-2H-1-benzopyran-2-carboxylic ethyl ester [Cohen et al. J. Med. Chem. 32, 1842–1860, (1989)] by the procedure described in the preceding preparation of Intermediate 2, in 98% yield as a yellow oil: MS (EI) m/e 270 (M+); $^1$H NMR (DMSO-d$_6$) δ 1.57–1.67 (1H, m), 1.92–1.98 (1H, m), 2.48–2.73 (2H, m), 3.51–3.61 (2H, m), 4.74 (1H, t, J=5.71 Hz), 5.02 (2H, s), 6.36 (1H, d, J=2.64), 6.46 (1H, dd, J=8.35, 2.64 Hz), 6.92 (1H, d, J=8.35 hz), 7.28–7.41 (5H, m).

Intermediate 4

(R,S)-3,4-Dihydro-7-methoxy-2H-1-benzopyran-2-methylbromide

To a solution of (R,S)-3,4-dihydro-7-methoxy-2H-1-benzopyran-2-methanol (3.14 g, 16.2 mmol) and carbontetrabromide (9.13 g, 28 mmol) in methylene chloride (50 ml) was slowly added a solution of triphenylphosphine (7.21 g, 27.5 mmol) in methylene chloride (50 mL) at 0° C. The reaction was allowed to warm to room temperature and stirred for 12 hours, then poured into water (150 mL) and extracted with methylene chloride (300 mL), dried and the solvent evaporated. Purification by chromatography (15% ethyl acetate/hexanes) afforded 3.16 g (75% yield) of a clear oil: IR (film) 2920, 1620, 1580, 1505, 1440, and 1160 cm−1; MS (EI) m/e, 258 (M+), 256 (M+); $^1$H NMR (CDCl$_3$) δ 1.84–1.93 (1H, m), 2.11–2.18 (1H, m), 2.72–2.80 (2H, m), 3.52 (1H, dd, J=10.54, 5.93 Hz), 3.59 (1H, dd, J=10.54, 5,49 Hz), 3.75 (3H, s), 4.18–4.24 (1H, m), 6.40 (1H, d, J=2.42 Hz), 6.45 (1H, dd, J=8.35, 2.64 Hz), 6.94 (1H, d, J=8.35 Hz).

Intermediate 5

(R,S)-3,4-Dihydro-7-(benzyloxy)-2H-1-benzopyran-2-methylbromide

This compound was prepared from (R,S)-3,4-dihydro-7-(benzyloxy)-2H-1-benzopyran-2-methanol according to the procedure employed in the preparation of Intermediate 4, in 60% yield as a white solid, mp 76°–78° C.

Elemental analysis for C$_{17}$H$_{17}$BrO$_2$ Calc'd: C, 61.28; H, 5.14. Found: C, 61.26; H, 5.04

Intermediate 6

[(7-Benzyloxy-chroman-2-ylmethyl)-2-napthalenyl-methyl]-amine

A solution of (R,S)-3,4-dihydro-7-(benzyloxy)-2H-1-benzopyran-2-methylbromide (1.14 g, 3.0 mmol) and 1-naphthalenemethylamine (1.41 g, 9.0 mmol) in anhydrous dimethyl sulfoxide (30 mL) were heated at 100° C. for 6 hours then poured into water (200 mL) and extracted with methylene chloride (2×150 mL). The combined organic layers were dried and the solvent removed under vacuum. Purification by flash chromatography (5% MeOH—CH$_2$Cl$_2$) afforded 930 mg (67% yield) of the title compound as a thick oil, MS EI m/e 409 (M+).

Intermediate 7

3-(7-Methoxy-chroman-2-ylmethyl-amino)-proponal

A mixture of (R,S)-3,4-dihydro-7-methoxy-2H-1-benzopyran-2-methylbromide (12.8 g, 49 mmol) and 1-amino-3-propanol (10 eq) were heated to 100° C. for 2 hours. The reaction mixture was washed with water (750 mLs) and extracted with methylene chloride (3×500 ml). The organic layer was dried over anhydrous magnesium sulfate, filtered, and the solvent evaporated to afford 11.3 g of desired product (92%). The oxalate salt was prepared from methanol, mp 180°–190° C.

Elemental analysis for C$_{14}$H$_{21}$NO$_3$.C$_2$H$_2$O$_4$ Calc'd: C, 56.30; H, 6.79; N, 4.10 Found: C, 55.92, H, 6.72: N, 4.10

This general procedure, utilizing benzylamine, 4-fluoro-benzylamine, 4-chlorobenzylamine, 4-methoxybenzylamine, N-methyl-benzylamine, phenylethylamine, phenylpropylamine and phenylbutylamine afforded:

Benzyl-(7-methoxy-chroman-2-ylmethyl)-amine (95%), as the oxalate salt, (1:1) quarter hydrate, mp 225°–226° C.

Elemental analysis for C$_{18}$H$_{21}$NO$_2$.C$_2$H$_2$O$_4$.0.25H$_2$O Calc'd: C, 63.56; H, 6.27; N, 3.71 Found: C, 63.63, H, 6.06: N, 3.87;

4-Fluoro-benzyl-(7-methoxy-chroman-2-ylmethyl)-amine (42%), MS EI m/e 301 (M+);

4-Chloro-benzyl-(7-methoxy-chroman-2-ylmethyl)-amine (59%), MS EI m/z 317, 319 (M+);

4-Methoxy-benzyl-(7-methoxy-chroman-2-ylmethyl)-amine (88%), mp 68°–70° C.

Elemental analysis for C$_{19}$H$_{23}$NO$_3$ Calc'd: C, 72.82; H, 7.40; N, 4.47 Found: C, 72.46, H, 7.36: N, 4.43;

Benzyl-methyl-(7-methoxy-chroman-2-ylmethyl)-amine (93%), EI MS m/e 297 (M+);

(7-Methoxy-chroman-2-ylmethyl)-(2-phenyl-ethyl)-amine (93%), as the oxalate salt, mp 223°–224° C.

Elemental analysis for Cl$_{19}$H$_{23}$NO$_2$.C$_2$H$_2$O$_4$ Calc'd: C, 65.10; H, 6.50; N, 3.62 Found: C, 64.91; H, 6.49: N, 3.66;

(7-Methoxy-chroman-2-ylmethyl)-(3-phenyl-propyl)-amine (99%), as the oxalate salt, quarter hydrate, mp 219°–220° C.

Elemental analysis for C$_{20}$H$_{25}$NO$_2$.C$_2$H$_2$O$_4$.0.25H$_2$O Calc'd: C, 65.82; H, 6.78; N, 3.49 Found: C, 65.09, H, 6.83: N, 3.45;

(7-Methoxy-chroman-2-ylmethyl)-(4-phenyl-butyl)-amine (90%), as the oxalate salt (1:1), mp 217°–218° C.

Elemental analysis for C$_{21}$H$_{27}$NO$_2$.C$_2$H$_2$O$_4$ Calc'd: C, 66.49; H, 7.03; N, 3.37 Found: C, 66.28, H, 6.95: N, 3.29.

Intermediate 8

(7-Methoxy-chroman-2-ylmethyl)-(3-phenoxy)-propyl]-amine

To a solution of 3-(7-methoxy-chroman-2-ylmethyl-amino)-propanol (2.0 g, 8.0 mmol), phenol (1.51 g, 16.0 mmol) and triphenylphosphine (4.19 g, 16 mmol) in anhydrous tetrahydrofuran (80 mL) was slowly added a solution of diisopropylazodicarboxylate (3.23 g, 16 mmol) in tetrahydrofuran (10 ml). The reaction was allowed to stir for 18 hours and was then quenched with water (200 mL), extracted with methylene chloride (3×150 mL) dried over anhydrous magnesium sulfate, filtered and the solvent removed under vacuum. Chromatography (1% methanol-ethyl acetate) afforded 1.66 g of product (63% yield) as a yellow oil. The oxalate salt was prepared by the addition of excess oxalic acid in warm methanol to a solution of the free base in warm methanol, mp 204°–205° C.

Elemental analysis for C$_{20}$H$_{25}$NO$_3$.C$_2$H$_2$O$_4$ Calc'd: C, 63.30; H, 6.52; N, 3.36 Found: C, 63.40; H, 6.51: N, 3.44

This general procedure utilizing 2-methyl-3-nitrophenol, 4-methyl-3-nitrophenol, 3-nitrophenol, and 4-chloro-3-nitrophenol afforded:

(7-Methoxy-chroman-2-ylmethyl)-[3-(2-methyl-3-nitrophenoxy)-propyl]-amine as the oxalate salt, quarter hydrate, (40%)

Elemental analysis for $C_{21}H_{26}N_2O_5 \cdot C_2H_2O_4 \cdot 0.25H_2O$
Calc'd: C, 57.43; H, 5.97; N, 5.82 Found: C, 57.39; H, 5.81: N, 5.81;

(7-Methoxy-chroman-2-ylmethyl)-[3-(4-methyl-3-nitro-phenoxy)-propyl]-amine (49%): IR (2900, 1630, 1580, 1525, and 1400 cm −1; MS m/e 386 (M+);

(7-Methoxy-chroman-2-ylmethyl)-[3-(3-nitro-phenoxy)-propyl]-amine, (52%), MS EI 372 (M+);

[3-(4-Chloro-3-nitro-phenoxy)-propyl]-(7-methoxy-chroman-2-ylmethyl)-amine oxalate salt (1:1), mp 215°–216° C., (17.6%);

Elemental analysis for $C_{20}H_{23}N_2O_5 \cdot C_2H_2O_4$ Calc'd: C, 53.18; H, 5.07; N, 5.64 Found: C, 52.91; H, 5.06: N, 5.33.

Intermediate 9

2-Chloro-5-{3-[7-methoxy-chroman-2-ylmethyl)-amino]-propoxy}phenylamine oxalate

To a mixture of [3-(4-chloro-3-nitro-phenoxy)-propyl]-(7-methoxy-chroman-2-ylmethyl)-amine (990 mg, 2.43 mmol) and hydrazine (156 rag, 4.87 mmol) in ethanol at 5° C. was added Raney nickel (400 mg). After 0.5 hour another portion of Raney nickel (300 mg) was added and the reaction was heated to reflux for 1 hour. The catalyst was filtered and the solvent removed to afford 800 mg of 2-chloro-5-{3-[7-methoxy-chroman-2-ylmethyl)-amino]-propoxy}phenylamine (87.4%). The oxalate salt was prepared in tetrahydrofuran, mp 219°–220° C.

Elemental analysis for $C_{20}H_{25}N_2O_3Cl \cdot (COOH)_2$ Calc'd: C, 56.59; H, 5.83; N, 5.95 Found: C, 56.40; H, 5.85; N, 5.95

Intermediate 10

(7-Methoxy-chroman-2-ylmethyl)-[3-(4-methyl-3-amino-phenoxy)-propyl]-amine

A solution of (7-methoxy-chroman-2-ylmethyl)-[3-(4-methyl-3-nitro-phenoxy)propyl]-amine (1.8 g, 4.7 mmol) in tetrahydrofuran (50 mL) containing 10% palladium on carbon (150 mg) was hydrogenated at 50 psi for 4 hours. The mixture was filtered through Celite®, washed with MeOH, and the solvent evaporated. The product was purified by chromatography (silica, 5% MeOH-methylene chloride) to afford 1.1 g (65 of a tan foam, MS EI m/e 356 (M+). The oxalate was prepared in isopropanol, mp 209°–213° C.

Elemental analysis for $C_{21}H_{28}NO_3 \cdot (COOH)_2 \cdot 0.25\ H_2O$
Calc'd: C, 61.25; H, 6.82; N, 6.21 Found: C, 61.14; H, 6.67; N, 6.08

Reduction of the nitro substituent of the corresponding precursor afforded the following compounds:

(7-Methoxy-chroman-2-ylmethhyl)-[3-(2-methyl-3-amino-phenoxy)propyl]-amine, (75%), MS EI m/e 356 (M+);

(7-Methoxy-chroman-2-ylmethyl)- [3-(3-amino-phenoxy)-propyl]-amine, (71%) MS EI m/e 342 (M+).

EXAMPLE 1

2-[(3-Phenoxy-propylamino)-methyl]-chroman-7-ol

A solution of (7-methoxy-chroman-2-ylmethyl)-(3-phenoxy-propyl)-amine (1.0 g, 3.1 mmol) in 48% aqueous HBr (40 mL) was heated to reflux for 4 hours. The reaction mixture was then allowed to cool to room temperature and basified with 1N sodium hydroxide until pH$_{12}$. The basic reaction mixture was extracted with ethyl acetate (2×100 mL), dried over anhydrous magnesium sulfate, filtered, and the solvent removed under vacuum. Chromatography (5% methanol in methylene chloride) afforded 0.5 g of product (52% yield) as a clear oil. The corresponding oxalate salt was prepared by the addition of a warm solution of excess oxalic acid in methanol (15 mL) to a solution of the free base in warm methanol (30 mL), mp 165°–166° C.

Elemental analysis for $C_{19}H_{23}NO_3 \cdot (COOH)_2 \cdot 0.5H_2O$
Calc'd: C, 61.15; H, 6.36; N, 3.40 Found: C, 61.01; H, 6.11; N, 3.35

This general demethylation procedure also afforded:

(1b) 2-[[3-(3-Amino-phenoxy)propylamino]methyl]-chroman-7-ol as the dihydrochloride, mp 163°–170° C. The dihydrochloride was produced by dissolving the free base in ethanol and adding an excess solution of HCl in diethyl ether. Upon concentration of the solution, crystals of the dihydrochloride formed and were recovered by filtration.

Elemental analysis for $C_{19}H_{24}N_2O_3 \cdot 2HCl$ Calc'd: C, 56.86; H, 6.68; N, 6.98 Found: C, 56.84; H, 6.71; N, 6.66

(1c) 2-{[3-(3-Amino-2-methyl-phenoxy)-propylamino]-methyl}-chroman-7-ol as the oxalate, hemihydrate, mp 196°–198° C.

Elemental analysis for $C_{20}H_{26}N_2O_3 \cdot (COOH)_2 \cdot 0.5H_2O$
Calc'd: C, 59.85; H, 6.62; N, 6.34 Found: C, 59.54; H, 6.41; N, 6.33

(1d) 2-{[3-(3-Amino-4-chloro-phenoxy)-propylamino]-methyl}-chroman-7-ol as the maleate, quarter hydrate, mp 153°–154° C., (72.0%). The maleate salt was formed by dissolving the free base in tetrahydrofuran and adding the resulting solution to a warm solution of maleic acid (2 eq.) in tetrahydrofuran. Upon cooling crystals formed and were dried and recovered by filtration.

Elemental analysis for $C_{19}H_{23}N_2O_3Cl \cdot C_4H_4O_4$ Calc'd: C, 57.14; H, 5.73; N, 5.79 Found: C, 57.08; H, 5.60; N, 5.73

(1e) 2-{[3-(3-Amino-4-methyl-phenoxy)-propylamino]-methyl}-chroman-7-ol as the oxalate salt (1:2), 0.33 hydrate, mp 186°–187° C.

Elemental analysis for $C_{20}H_{23}N_2O_3 \cdot 2(COOH)_2 \cdot 0.33H_2O$
Calc'd: C, 54.55; H, 5.85; N, 5.30 Found: C, 54.26; H, 5.71; N, 5.04

(1f) 2-(Benzylamino-methyl)-chroman-7-ol as the oxalate, hemihydrate, mp 176°–177° C.

Elemental analysis for $C_{17}H_{19}NO_2 \cdot (COOH)_2 \cdot 0.5H_2O$
Calc'd: C, 61.94; H, 6.02; N, 3.80 Found: C, 61.81; H, 5.86; N, 3.84

(1g) 2-[(Benzyl-methyl-amino)-methyl]-chroman-7-ol as the oxalate salt, 179°–180° C.

Elemental analysis for $C_{18}H_{21}NO_2 \cdot (COOH)_2$ Calc'd: C, 64.33; H, 6.21; N, 3.75 Found: C, 64.02; H, 6.07; N, 3.67

(1h) 2-(4-Fluoro-benzylamino-methyl)-chroman-7-ol as the oxalate, hemihydrate, (54%), mp 165°–166° C.

Elemental analysis for $C_{17}H_{18}NFO_2 \cdot (COOH)_2$ Calc'd: C, 60.47; H, 5.34; N, 3.71 Found: C, 60.37; H, 5.39; N, 3.49

(1i) 2-(4-Chloro-benzylamino-methyl)-chroman-7-ol as the oxalate, hemihydrate, mp 179°–180° C.

Elemental analysis for $C_{17}H_{18}NClO_2 \cdot (COOH)_2$ Calc'd: C, 57.95; H, 5.62; N, 3.56 Found: C, 57.51; H, 5.85; N, 3.39

(1j) 2-(4-Hydroxy-benzylamino-methyl)-chroman-7-ol as the oxalate, quarter hydrate, mp 188°–89° C.

Elemental analysis for $C_{17}H_{19}NO_3 \cdot (COOH)_2 \cdot 0.25H_2O$
Calc'd: C, 60.07; H, 5.70; N, 3.69 Found: C, 60.03; H, 5.38; N, 3.60

(1k) 2-(Phenethylamino-methyl)-chroman-7-ol as the oxalate, quarter hydrate, mp 194°–195° C.

Elemental analysis for $C_{18}H_{21}NO_2 \cdot (COOH)_2 \cdot 0.25H_2O$
Calc'd: C, 63.56; H, 6.02; N, 3.71 Found: C, 63.55; H, 6.17; N, 3.63

(1l) 2-[(3-Phenyl-propylamino)-methyl]-chroman-7-ol as the oxalate, hydrate (2:1), mp 270°–290° C. (dec).

Elemental analysis for $C_{19}H_{23}NO_2 \cdot 0.5(COOH)_2 \cdot 1.0 H_2O$ Calc'd: C, 66.64; H, 7.27; N, 3.89 Found: C, 66.57; H, 6.74; N, 3.88

(1m) 2-[(4-Phenyl-butylamino)-methyl]-chroman-7-ol as the oxalate salt (2:1), mp 227°–228° C.

Elemental analysis for $C_{20}H_{25}NO_2 \cdot 0.5(COOH)_2$ Calc'd: C, 70.76; H, 7.35; N, 3.93 Found: C, 70.42; H, 7.31; N, 3.78

EXAMPLE 2

2-[(Napthalen-1-ylmethyl)-amine-methyl]-chroman-7-ol

A solution of [(7-benzyloxy-chroman-2-ylmethyl)-2-napthalenyl-methyl]-amine (930 mg, 2.3 mmol) in tetrahydrofuran (50 mL) containing 10% palladium on carbon (500 mg) was hydrogenated at 50 psi for 12 hours. The mixture was filtered through Celite®, washed with MeOH, and the solvent evaporated. The product was purified by chromatography (silica, 3% MeOH-methylene chloride) to afford 300 mg (41%) of a tan foam. The oxalate was prepared in isopropanol, mp 113°–114° C.

Elemental analysis for $C_{21}H_{21}NO_2 \cdot (COOH)_2$ Calc'd: C, 67.47; H, 5.66; N, 3.42 Found: C, 67.77; H, 5.73; N, 3.52

EXAMPLE 3

Resolution of (±)-2-(Benzylamino-methyl)-chroman-7-ol (±)-2-(Benzylamino-methyl)-chroman-7-ol (400 mg), compound (1 f) supra. was submitted to semipreparative HPLC containing a Chiralcel OJ® column and eluted (10 mL/min, pressure 430 psi, detection at 280 nm) with a hexane/EtOH (1:1) mixture. The first peak at 8.7 minutes was collected to afford (−)-2-(benzylamino-methyl) chroman-7-ol (103 mg) as a clear thick oil (99.5% optical purity). $[\alpha]25°-107°$ (c 1.01, CHCl$_3$). The (−)-free base was treated with excess oxalic acid in THF to afford 118 mg of the oxalate salt, mp 212°–213° C., $[\alpha]25°-76°$, c 1.03, DMSO). Optical purity observed to be 99.5% by HPLC (acetonitrile-1M sodium perchlorate, 1:1, 0.5 mL/min, 280 nM). The second peak isolated with a retention time of 10.15 minutes was collected to afford the (+)-2-(benzylamino-methyl)-chroman-7-ol (174 mg) as a clear thick oil (99.9% optical purity): $[\alpha]25°+104°$ (c, 1.15, CHCl$_3$). Optical purity observed to be 99.9% (acetonitrile-1M sodium perchlorate, 1:1, 0.5 mL/min, 280 nM). The (+)-free base was treated with excess oxalic acid in THF to afford 175 mg of the oxalate salt, mp 212°–213° C., $[\alpha]^{25}+82°$ (c 1.00, DMSO).

EXAMPLE 4

2-(Benzylamino-methyl)-chroman-6-chloro-7-ol

To a solution of 3,4-dihydro-7-methoxy-2H-1-benzopyran-2-methanol (23 g, 0.118 mol) in anhydrous pyridine (500 mL) was added p-toluenesulfonyl chloride (33.9 g, 0.78 mol). The reaction was allowed to stir for 2 days under nitrogen at room temperature then the solution was concentrated under vacuum. The crude product was diluted with $CH_2Cl_2$ (1 L) and washed with 1M $H_2SO_4$ (2×500 mL). The organic layer was washed with saturated aqueous sodium bicarbonate (1 L), brine (500 mL) and the organic layer dried and concentrated under vacuum to afford 34 g (92.2% yield) of (R,S)-3,4-dihydro-7-methoxy-2H-1-benzopyran-2-methyltosylate as a white solid: mp 67°–69° C.; MS (EI) m/z 348 (M+); $^1$H NMR (DMSO-d$_6$) d 1.51–1.65 (1H, m), 1.84–1.90 (1H, m), 2.41 (3H, s), 2.53–2.70 (2H, m), 3.66 (3H, s), 4.16 (1H, m), 4.26 (1H, m), 6.18 (1H, d, J=2.42 Hz), 6.38 (1H, dd, J=8.35, 2.64 Hz), 6.90 (1H, d, J=8.35), 7.48 (2H, d, J=8.57 Hz), 7.82 (2H, d, J=8.35).

A solution of (R,S)-3,4-dihydro-7-methoxy-2H-1-benzopyran-2-methyltosylate(1.32 g, 3.79 mmol) and N-chlorosuccinimide (607 mg, 4.54 mmol) in anhydrous THF (12 mL) was allowed to stir at room temperature for 40 hours then poured into diethyl ether (200 mL). The organic layer was washed with water (100 mL) and dried over anhydrous magnesium sulfate, filtered, and the solvent removed under vacuum. Purification by chromatography (10% ethyl acetate-hexanes) afforded 1.37 g (94.4%) of (R,S)-3,4-dihydro-6-chloro-7-methoxy-2H-1-benzopyran-2-methyltosylate as a white solid. Recrystallization from ethyl acetate provided an analytical sample: mp 114°–115° C. (EtOAc); MS (EI) m/e 382/384 (M+).

Elemental analysis for $C_{18}H_{19}ClO_5S$ Calc'd: C, 56.47; H, 5.00 Found: C, 56.57; H, 4.94

A mixture of (R,S)-3,4-dihydro-6-chloro-7-methoxy-2H-1-benzopyran-2-methyltosylate (1.97 g, 5.15 mmol) and benzylamine (1.66 g, 15.4 mmol) in anhydrous dimethylsulfoxide (12 mL) was heated to 80° C. for 30 hours then poured into water (100 mL) and extracted with methylene chloride (2×200 mL). The organic layer was dried and the solvent removed under vacuum. Purification by chromatography (5% methanol-methylene chloride) afforded a 1.48 g (90.4%) of (±)-benzyl-(7-methoxy-6-chloro-chroman-2-ylmethyl)-amine as a clear oil; MS EI m/e 315/317 (M+); HRMS 317.1182 calc'd for $C_{18}H_{20}NO_2Cl$ found 317.1101.

(±)-Benzyl-(7-methoxy-6-chloro-chroman-2-ylmethyl)-amine. (1.41 g, 4.43 mmol) was treated with HBr as decribed above in Example 1 to afford 1.20 g (89.2%) of (±)-2-(Benzylamino-methyl)-chroman-6-chloro-7-ol as a yellow solid: mp 151°–152 ° C. The fumarate salt was prepared in isopropanol: MS EI 303/305 m/e (M+).

Elemental analysis for $C_{17}H_{18}NO_2Cl \cdot C_4H_4O_4$ Calc'd; C, 60.08; H, 5.28; N, 3.34 Found; C, 60.04; H, 5.18; N, 3.33.

EXAMPLE 5

Resolution of (±)-2-(Benzylamino-methyl)-6-chloro-chroman-7-ol

Racemic (±)-2-(Benzylamino-methyl)-6-chloro-chroman-7-ol (731 mg) was resolved on a Chiralcel OJ column (10 mL/min, pressure 430 psi, detection at 290 nm) by collecting fractions from forty separate runs using approximately 18 mg per injection to intitally afford the levorotary isomer (322 mg, 8.9 min) as a light tan solid (optical purity determined to be 99.9%): mp 118°–119° C.; $[\alpha]^{25}_D-124.0°$ (c=1.0. CHCl$_3$). The (−)-free base was converted to its fumarate salt in isopropanol to afford a white crystalline solid: mp 214°–215° C.; $[\alpha]^{25}_D-69.0$ (c=1.0, DMSO). Chemical purity determined to be 97.6% pure by HPLC and optical purity determined to be 99.8%.

Elemental analysis for $C_{17}H_{18}ClNO_2 \cdot C_4H_4O_4$ Calc'd; C, 60.08; H, 5.28; N, 3.34 Found; C, 59.71; H, 5.15; N, 3.16.

The second peak isolated having a retention time of 10.9 minutes was collected to afford the dextrorotary isomer (321 mg) as a light pinkish solid (optical purity determined to be 99.7%): mp 116°–118° C.; $[\alpha]^{25}_D+120.0°$ (c=1.0, CHCl$_3$). The fumarate salt was prepared in isopropanol to afford a white crystalline solid: mp 211°–212.5° C.; $[\alpha]^{25}_D+68.1$ (c=1.0, DMSO). Chemical purity determined to be 100.0% and optical purity found to be 99.5%.

Elemental analysis for $C_{17}H_{18}ClNO_2 \cdot C_4H_4O_4$ Calc'd; C, 60.08; H, 5.28; N, 3.34 Found; C, 60.16; H, 5.20; N, 3.28.

The compounds of this invention are dopamine autoreceptor agonists, that is, they serve to modulate the synthesis and release of the neurotransmitter dopamine. They are thus useful for treatment of disorders of the dopaminergic system, such as schizophrenia, Parkinson's disease and Tourette's syndrome. Such agents are partial agonists at the postsynaptic dopamine $D_2$ receptor and are thereby useful in the treatment of alcohol and drug addiction.

Affinity for the dopamine autoreceptor was established by a modification of the standard experimental test procedure of Seemen and Schaus, European Journal of Pharmacology 203: 105–109, 1991, wherein homogenized rat striatal brain tissue is incubated with $^3$H-quinpirole (Quin.) and various concentrations of test compound, filtered and washed and counted in a Betaplate scintillation counter.

High affinity for the dopamine D-2 receptor was established by the standard experimental test procedure of Fields, et al., Brain Res., 136, 578 (1977) and Yamamura et al., eds., Neurotransmitter Receptor Binding, Raven Press, N.Y. (1978) wherein homogenized limbic brain tissue is incubated with $^3$H-spiroperidol (Spiper.) and various concentrations of test compound, filtered and washed and shaken with Hydrofluor scintillation cocktail (National Diagnostics) and counted in a Packard 460 CD scintillation counter.

The results of the tests with compounds representative of this invention are given in the immediately following table. Analogous compounds devoid of the 7-hydroxy group are exemplified in the next table, to illustrate the markedly improved agonistic potency attending the 7-hydroxy substituted modification.

in the treatment of dopaminergic disorders such as schizophrenia, Parkinson's Disease, Tourette's Syndrome, alcohol addiction, cocaine addiction, and addiction to analagous drugs.

Applicable solid carriers for pharmaceutical compositions containing the compounds of this invention can include one or more substances which may also act as flavoring agents, lubricants, solubilizers, suspending agents, fillers, glidants, compression aids, binders or tablet-disintergrating agents or an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers may be used in preparing solutions, suspensions, emulsions, syrups and elixirs. The active ingredient of this invention can be dissolved or suspended in a pharmaceutically acceptable liquid carrier such as water, an organic solvent, a mixture of both or pharmaceutically acceptable oils or fat. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as

| Example No. | IC$_{50}$ (nM) D2 Quin. | IC$_{50}$ (nM) D2 Spiper. | IC$_{50}$ (nM) 5-HT$_{1a}$ | IC$_{50}$ (nM) α$_1$ | Ratio |
|---|---|---|---|---|---|
| 1 | 1.11 | 91 | 2.78 | 18 | 82 |
| 1b | 1.4 | 789 | 5.1 | 76 | 563 |
| 1c | 2.0 | 245 | 1.13 | 19 | 122 |
| 1d | 0.42 | 243 | 1.9 | 36 | 578 |
| 1e | 9.12 | 385 | 2.09 | 36 | 42.2 |
| 1f | 0.42 | 122 | 104 | 1145 | 290 |
| 1g | 9.66 | 780 | 385 | 1622 | 81 |
| 1h | 1.70 | 880 | 143 | 2884 | 518 |
| 1i | 0.61 | 322 | 87 | 1247 | 527 |
| 1j | 1.25 | 206 | 63 | 1007 | 165 |
| 1k | 1.59 | 422 | 14 | 86 | 266 |
| 1l | 0.71 | 206 | 7.21 | 127 | 291 |
| 1m | 1.09 | 61 | 2.79 | 80 | 56 |
| 2 | 2.25 | 71.3 | 121.0 | 72.0 | 24 |
| 3 | 0.26 | 53.3 | 45 | 423 | 205 |
| 3 | 26.2 | 1132 | 1980 | 3248 | 70 |
| 4 | 1.97 | 91 | | | 46 |
| 5(−) | 1.46 | 35 | | | 24 |
| 5(+) | 87.9 | 421.9 | | | 4.8 |
| [structure: chroman-CH$_2$-NH-CH$_2$-phenyl] | 115 | — | 119 | 630 | — |
| [structure: chroman-CH$_2$-NH-CH$_2$-phenyl-F] | 147 | — | 92 | 1282 | — |

Hence, the compounds of this invention effect the synthesis of the neurotransmitter dopamine and thus are useful above e.g. cellulose derivatives, preferably sodium carboxymethyl cellulose solution), alcohols (including monohydric alcohols and polyhydric alcohols e.g. glycols) and their derivatives, and oils (e.g. fractionated coconut oil and arachis oil). For parenteral administration the carrier can also be an oily ester such as ethyl oleate and isopropyl myristate. Sterile liquid carriers are used in sterile liquid form compositions for parenteral administration.

Liquid pharmaceutical compositions which are sterile solutions or suspensions can be utilized by, for example, intramuscular, intraperitoneal or subcutaneous injection. Sterile solutions can also be administered intravenously. Oral administration may be either liquid or solid composition form.

Preferably the pharmaceutical composition is in unit dosage form, e.g. as tablets or capsules. In such form, the composition is sub-divided in unit dose containing appropriate quantities of the active ingredient; the unit dosage forms can be packaged compositions, for example packeted powders, vials, ampoules, prefilled syringes or sachets containing liquids. The unit dosage form can be, for example, a capsule or tablet itself, or it can be the appropriate number of any such compositions in package form.

The dosage to be used in the treatment of a specific psychosis must be subjectively determined by the attending physician. The variables involved include the specific psychosis and the size, age and response pattern of the patient.

What is claimed is:

1. A compound of the formula:

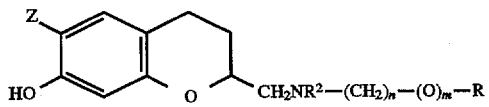

in which
Z is hydrogen or a halogen;
n is one of the integers 1, 2, 3,or 4;
m is one of the integers 0 or 1;
R is

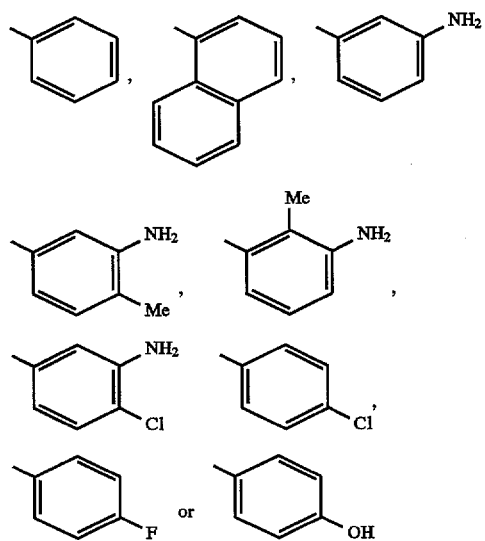

$R^2$ is hydrogen or alkyl of 1 to 3 carbon atoms; or a pharmaceutically acceptable salt thereof.

2. The compound of claim 1 which is 2-[(3-(phenoxy) propylamino)-methyl]-chroman-7-ol or a pharmaceutically acceptable salt thereof.

3. The compound of claim 1 which is 2-{[3-(3-aminophenoxy)propylamino]-methyl}-chroman-7-ol or a pharmaceutically acceptable salt thereof.

4. The compound of claim 1 which is 2-{[3-(3-amino-2-methyl-phenoxy)propylamino]-methyl}-chroman-7-ol or a pharmaceutically acceptable salt thereof.

5. The compound of claim 1 which is 2-{[3-(3-amino-4-chloro-phenoxy)propylamino]-methyl}-chroman-7-ol or a pharmaceutically acceptable salt thereof.

6. The compound of claim 1 which is 2-{[3-(3-amino-4-methyl-phenoxy)propylamino]-methyl}-chroman-7-ol or a pharmaceutically acceptable salt thereof.

7. The compound of claim 1 which is 2-(benzylamino-methyl)-chroman-7-ol or a pharmaceutically acceptable salt thereof.

8. The compound of claim 1 which is (−)-2-(benzylamino-methyl)-chroman-7-ol or a pharmaceutically acceptable salt thereof.

9. The compound of claim 1 which is (+)-2-(benzylamino-methyl)-chroman-7-ol or a pharmaceutically acceptable salt thereof.

10. The compound of claim 1 which is 2-[(benzyl-methyl-amino)-methyl]-chroman-7-ol or a pharmaceutically acceptable salt thereof.

11. The compound of claim 1 which is 2-(4-fluoro-benzylamino-methyl)-chroman-7-ol or a pharmaceutically acceptable salt thereof.

12. The compound of claim 1 which is 2-(4-chloro-benzylamino-methyl)-chroman-7-ol or a pharmaceutically acceptable salt thereof.

13. The compound of claim 1 which is 2-(4-hydroxy-benzylamino-methyl)-chroman-7-ol or a pharmaceutically acceptable salt thereof.

14. The compound of claim 1 which is 2-(phenethylamino-methyl)-chroman-7-ol or a pharmaceutically acceptable salt thereof.

15. The compound of claim 1 which is 2-[(3-phenyl-propylamino)-methyl]-chroman-7-ol or a pharmaceutically acceptable salt thereof.

16. The compound of claim 1 which is 2-[(4-phenyl-butylamino)-methyl]-chroman-7-ol or a pharmaceutically acceptable salt thereof.

17. The compound of claim 1 which is 2-[(naphthaten-1-ylmethyl)-amino-methyl]-chroman-7-ol or a pharmaceutically acceptable salt thereof.

18. The compound of claim 1 which is 2-(benzylamino-methyl)-chroman-6-chloro-7-ol or a pharmaceutically acceptable salt thereof.

19. The compound of claim 1 which is (+)-2-(benzylamino-methyl)-chroman-6-chloro-7-ol or a pharmaceutically acceptable salt thereof.

20. The compound of claim 1 which is (−)-2-(benzylamino-methyl)-chroman-6-chloro-7-ol or a pharmaceutically acceptable salt thereof.

* * * * *